(12) United States Patent
Coleman et al.

(10) Patent No.: US 6,315,727 B1
(45) Date of Patent: Nov. 13, 2001

(54) METHOD AND APPARATUS FOR ULTRASOUND CORNEAL SCANNING

(75) Inventors: D. Jackson Coleman, Haworth, NJ (US); Dan Z. Reinstein, Vancouver (CA); Ronald H. Silverman, Nyack, NY (US)

(73) Assignee: Cornel Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/408,256

(22) Filed: Sep. 29, 1999

(51) Int. Cl.[7] ................................................. A61B 8/02
(52) U.S. Cl. ...................................................... 600/452
(58) Field of Search .................................. 351/200, 212; 600/444, 452, 443, 447

(56) References Cited

U.S. PATENT DOCUMENTS 5,331,962 * 7/1994 Coleman et al. ................ 600/444

* cited by examiner

*Primary Examiner*—George Manuel
(74) *Attorney, Agent, or Firm*—Abelman, Frayne & Schwab

(57) ABSTRACT

An improved method and apparatus for conducting biometric high frequency ultrasound scanning of the human eye permits the subject to assume a seated position and to place the eye to be scanned in contact with the fluid medium contained in an eye cup. In a prefered embodiment, the eye cup is disposable after each use.

25 Claims, 4 Drawing Sheets

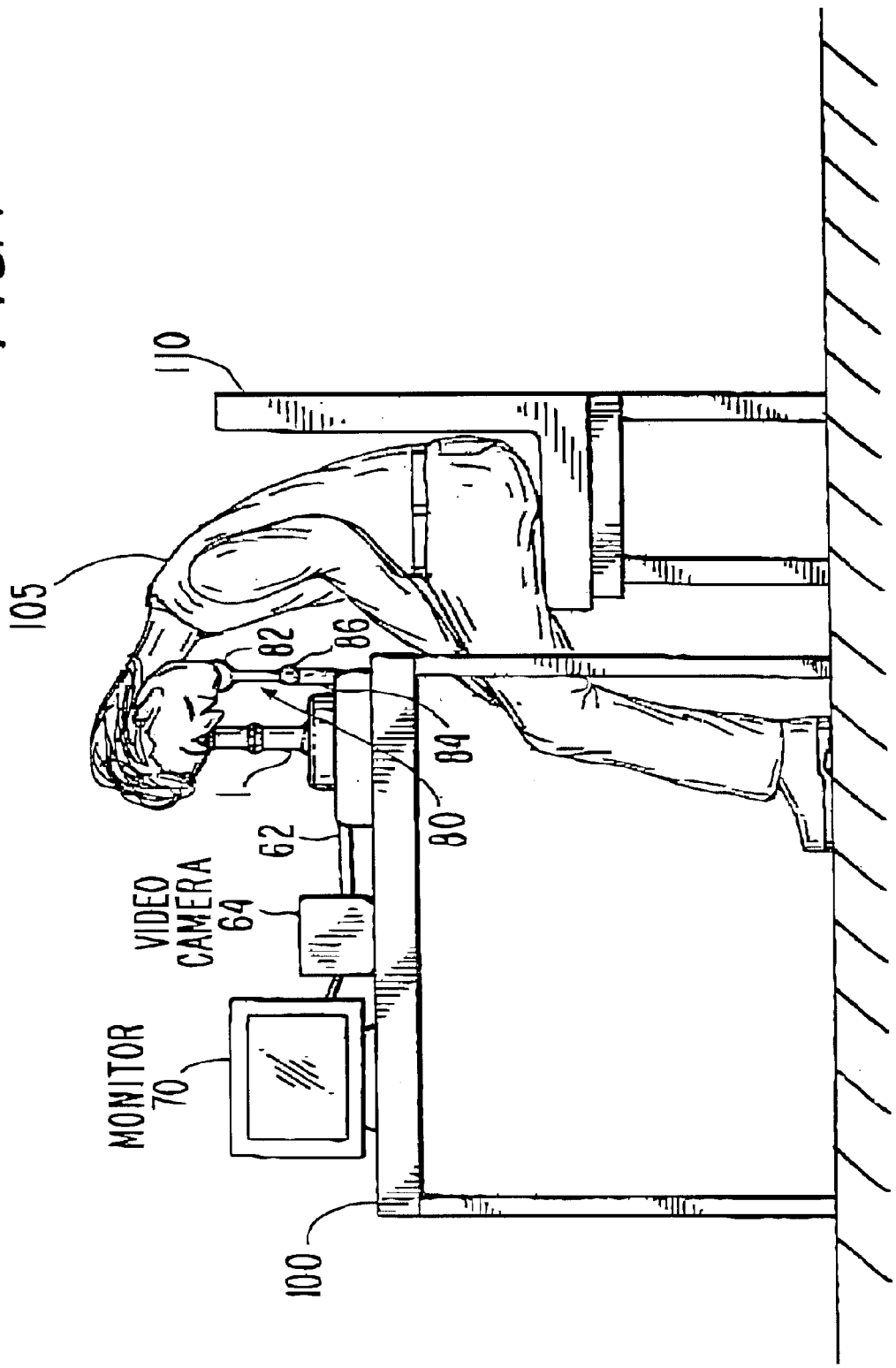

METHOD AND APPARATUS FOR ULTRASOUND CORNEAL SCANNING

FIELD OF THE INVENTION

This invention relates to ophthalmic apparatus and methods for performing ultra-high frequency and very high frequency ultrasound scans of the human cornea.

BACKGROUND OF THE INVENTION

In order to perform a high frequency (HF) ultrasound scan of the cornea, it is necessary to provide a conductive medium between the moving transducer which generates the ultrasound waves and the surface of the cornea under examination. The preferred medium is a balanced salt solution which has the same osmolarity as the tears in the eye in order to prevent corneal edema.

At present, there are two principle types of HF ultrasound scanning apparatus. In an apparatus that is designed to obtain highly accurate biometric data for the purposes of producing computer-generated images of the structure and topography of the cornea and adjacent surfaces, the subject is required to lie supine on an examination table so that the apparatus can be positioned over the patient's upwardly facing eyes. In order to establish a liquid bath above the cornea into which the tip of the transducer can be immersed, a water-tight dam or drape must be established around the eye. This is typically done by securing the interior surface of an annular sheet of flexible polymeric material to the skin around the subject's eye using a physiologically compatible adhesive. The exterior periphery of the flexible polymeric dam must then be retained in an upstanding and outwardly extending position, as by securing it in a stationary double-ring clamp. The subject's eye is treated with an anesthetic and the eyelids are maintained in an open position by means of a lid speculum. Thereafter, the dam around the eye is filled with a normal saline solution to a depth of approximately 2 cm above the cornea so that the movable transducer tip can be immersed for scanning movement beneath the surface of the saline bath. The procedure is described in more detail in U.S. Pat. Nos. 5,293,811 and 5,369,454.

The length of time required to complete the scanning depends upon the nature and extent of the data required to prepare the images. In some case, only a few minutes is required to complete the scan, while the time required to prepare the subject for the procedure is much more extensive. Moreover, once the procedure has been completed, the dam must be pulled away from the subject's skin and the adhesive material removed. In most cases, the same procedure is repeated on the other eye, and the level of anxiety and discomfiture of the subject may be increased. The use of a flexible dam that has to be secured to the epidermal area around the eye necessarily requires a substantial amount of balanced saline solution and requires more time for clean-up and leads to inevitable spills of liquid on the subject, the technician and/or examining room equipment.

In a second type of apparatus that is in common use, the subject is seated upright in a chair with his/her head tilted back against a headrest; the subject's eye is anesthetized and the eyelids retained in an open position by a lid speculum; and an eye cup is placed in direct contact with the surface of the eyeball. The eye cup is filled with a balanced saline solution and a transducer attached to a flexible cable is manually inserted into the solution and moved to obtain the data required for the scan. It will be understood that this apparatus and method is far less capable of generating data from the whole cornea for producing biometric images. It is also somewhat more stressful for the subject, since despite the anesthetic, the presence of the eye cup in the eye induces a higher level of anxiety.

It is therefore an object of this invention to provide a method and apparatus for the high frequency ultrasound scanning where the human cornea is immersed in a liquid transmission medium that does not require adhesives or other means for semi-permanently attaching retaining means to contain the liquid medium.

It is another object of this invention to provide a method and apparatus for accomplishing ultrasound corneal scans that is more comfortable and less stressful for the subject than the procedures that are currently available.

It is yet another object of this invention to provide an apparatus in which the subject can sit comfortably and properly position his/her own eye in an eye cup containing the liquid medium through which the ultrasound waves are transmitted to accomplish the corneal scan.

A further object of the invention is to provide an apparatus in which the position of the subject's cornea with respect to the eye cup can be monitored by a video image employing a camera having a lens proximate the bottom of the eye cup.

Another object of this invention is to provide for multi-planar, spiral or meridional data collection for use in three-dimensional reconstruction and for volume measurement.

It is also an object of the invention to provide an improved method and apparatus for more efficiently accomplishing ultrasonic corneal scans that requires minimal preparation of the subject and less time to complete the preparation and the scan.

Further objects of the invention are to provide an improved apparatus and method employing a relatively inexpensive disposable and sterilizable eye cup that is discarded after use by each subject and that is replaced with a fresh sterile eye cup.

SUMMARY OF THE INVENTION

The above objects and other advantages are achieved by the improved method and apparatus of the current invention in which the biometric high frequency ultrasound scanning apparatus for scanning a human subject's cornea is mounted in a supporting housing with the transducer element pointing upwardly in a generally vertical position, providing a fluid-tight seal around the proximate tip of the transducer, which seal extends to the base of an upwardly opening eye cup the walls of which eye cup terminate above the emitting end of the transducer. The eye cup is adapted to receive and contain a balanced saline solution in secure fluid-tight relation. The surface of the upper peripheral edge of the cup is configured to engage the eye so that the subject's cornea is immersed in the solution.

In a preferred embodiment, the apparatus with the upwardly opening eye cup is securely supported on stable, horizontal surface, such as a table or a like structure, at an appropriate height to accommodate a subject that is seated on a chair, stool or other specially-designed seating means that will allow the subject to assume a relaxed position in which the head can be comfortably lowered to place the eye over the eye cup.

In an especially preferred embodiment of the invention, the eye cup is fabricated from a light-weight material, such as molded plastic, that can be sterilized. In a most preferred embodiment, the eye cup is disposable and the apparatus further includes a support for the eye cup.

From the above, it will be understood that the subject need not assume a supine position on an examination table, but rather will assume a normal seated position before the apparatus, which in itself will reduce the anxiety level and discomfiture of many individuals. The subject also has a greater sense of control in that the subject will move her head into the appropriate position on the eye cup, which will further increase the comfort level and confidence of the subject. With the improved apparatus of the invention, a minimal quantity of saline solution is required, and there is no opportunity for spilling of the fluid on the subject or examination room equipment during the procedure.

The improved apparatus and method also provides for an enhanced level of sterility, which is of especial importance where the subject is undergoing the ultrasonic scanning as a preoperative laser surgical procedure or for possible post-trauma or surgical studies.

BRIEF DESCRIPTION OF THE DRAWINGS

The invention will be further described with reference to the attached drawings in which like elements are referred to using the same numbers, and where

FIG. 4 is a side elevational view illustrating the use of the eye cup of the invention while the subject is in a seated position.

DETAILED DESCRIPTION OF THE INVENTION

Figure 1:
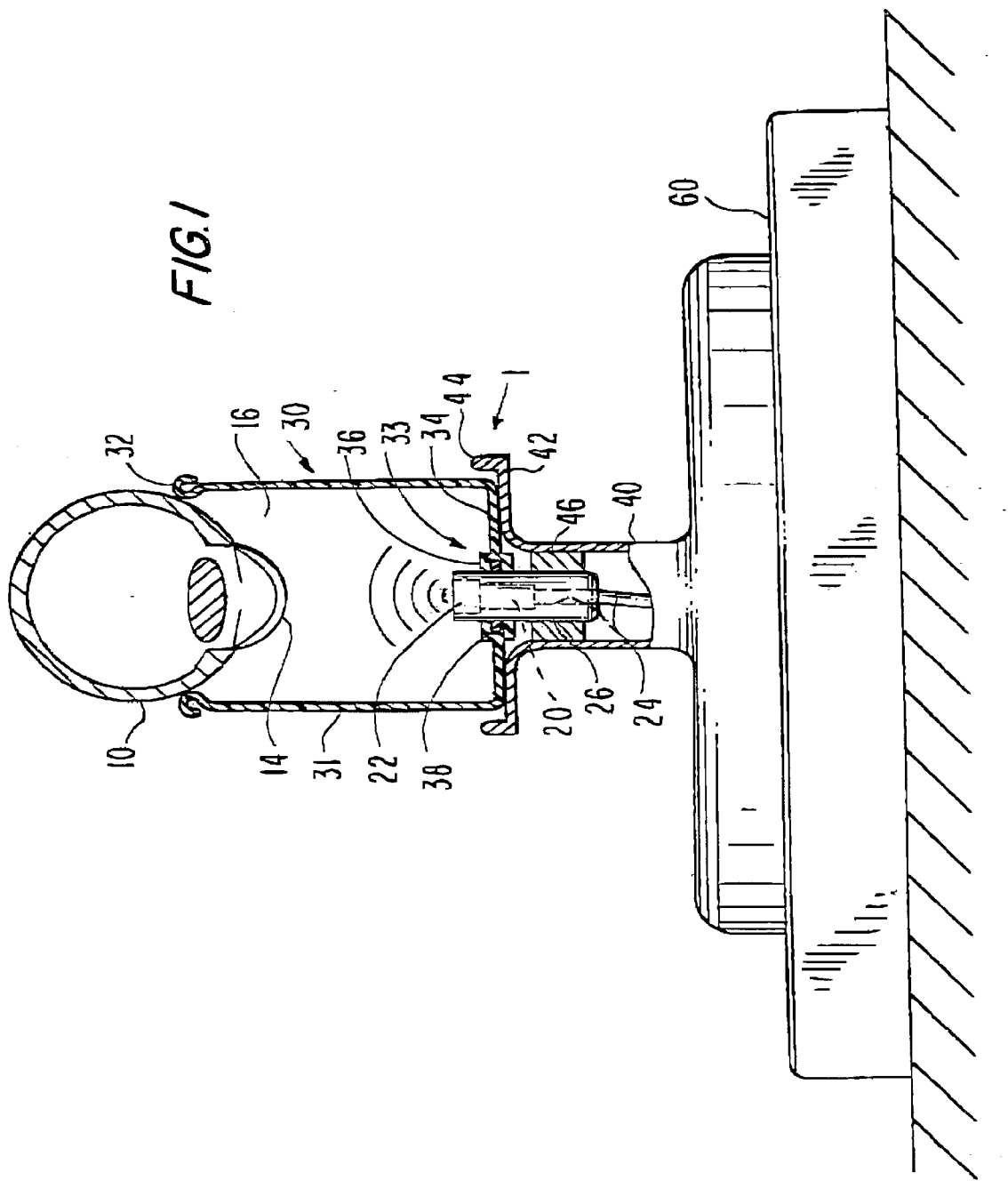
FIG. 1 is a side elevation view, partly in cross-section, schematically illustrating one preferred embodiment of the invention.

Referring to the schematic representation of FIG. 1, the subject's eye (10) that is to be scanned is brought into position from above the improved apparatus of the invention that is referred to generally as 1. The cornea (14) is immersed in conductive liquid (16) which is a physiologically compatible saline solution or other acceptable ophthalmic solution.

In the embodiment of FIG. 1, the conductive solution is also in contact with transducer (20) which is maintained in a fixed, upwardly facing vertical position inside of transducer housing (26). The transducer receives its power and control signals through conductors (24) from appropriate control circuitry (not shown). The transducer emitting element (22) is positioned just below the rim of the housing (26) and when activated, produces the ultra high frequency waves that are conducted via the liquid (16) and then reflected back by the corneal structure and surrounding tissue. The reflected waves are converted into digitized data that is processed by means of software that is known in the art to produce visual images on a monitor and/or in printed form.

As further shown in FIG. 1, an eye cup (30) of novel construction comprises continuous sidewall (30), which in a preferred embodiment is of generally oval cross section. The upper end of the sidewall (31) terminates in rim (32) that is configured to receive the surface of the eye (10) surrounding the globe (cornea) (16) in close-fitting relation.

In the practice of the invention, the subject's eye is temporarily anesthetized with topical anesthetic drops and may be held open voluntarily by the subject or by means of a lid speculum. The subject is preferably seated comfortably before the apparatus and lowers her head by bending at the neck to bring the fornices of the eye into contact with the rim (32) of the eye cup (30) that has been filled with a sterile saline solution or other acceptable fluid.

The bottom wall (34) of the eye cup (30) can be formed integrally with sidewall (31), the bottom wall terminating in a cup base mounting member (33). In the embodiment of FIG. 1, the cup base mounting member (33) comprises an aperture (35) that is defined by gasket retaining means (36). As shown in the cross-section of FIG. 1, gasket retaining means (36) is preferably fitted with an o-ring gasket that produces a fluid-tight seal with the exterior surface of transducer housing (26). As will be understood from the drawing, it is preferred that the transducer housing and aperture are of circular cross section and share a common central axis.

With continued reference to FIG. 1, it will be seen that cup (30) is retained on cup support (40) and integral supporting platform (42), which preferably terminates in an upturned edge flange (44) that engages the base and sidewall of eye cup (30) to securely retain it in position against any forces applied during handling and while the subject's eye is in contact with the fluid inside the cup. In a further preferred embodiment, not shown, the sidewalls and/or base of the eye cup (30) are provided with lugs and the supporting platform (42) and/or upturned flange (44) are provided with channels for receiving the lugs to securely lock the eye cup into position on the support (40).

As also shown in the cross-sectional view of FIG. 1, transducer housing (26) is held in a secure and vertically aligned position in the interior of cup support (40) by a housing retainer, which can take the form of a bushing (46), set screws (not shown), or other mechanical retaining means. When cup (30) is removed from the support, access to the transducer housing 26 and emitting element 22 is easily accomplished, in order to facilitate transducer replacement or maintenance of this part of the apparatus.

Cup support (40) can be formed integrally with or securely attached to a base unit or cabinet (60) that in turn can be secured to a table or the surface of other examining room equipment. Base unit or cabinet (60) can also be provided with additional ballast to stabilize the apparatus. The electrical components and circuitry required to power the transmitter, receiver and auxiliary elements that will described below are conveniently assembled within cabinet (60).

Figure 2:
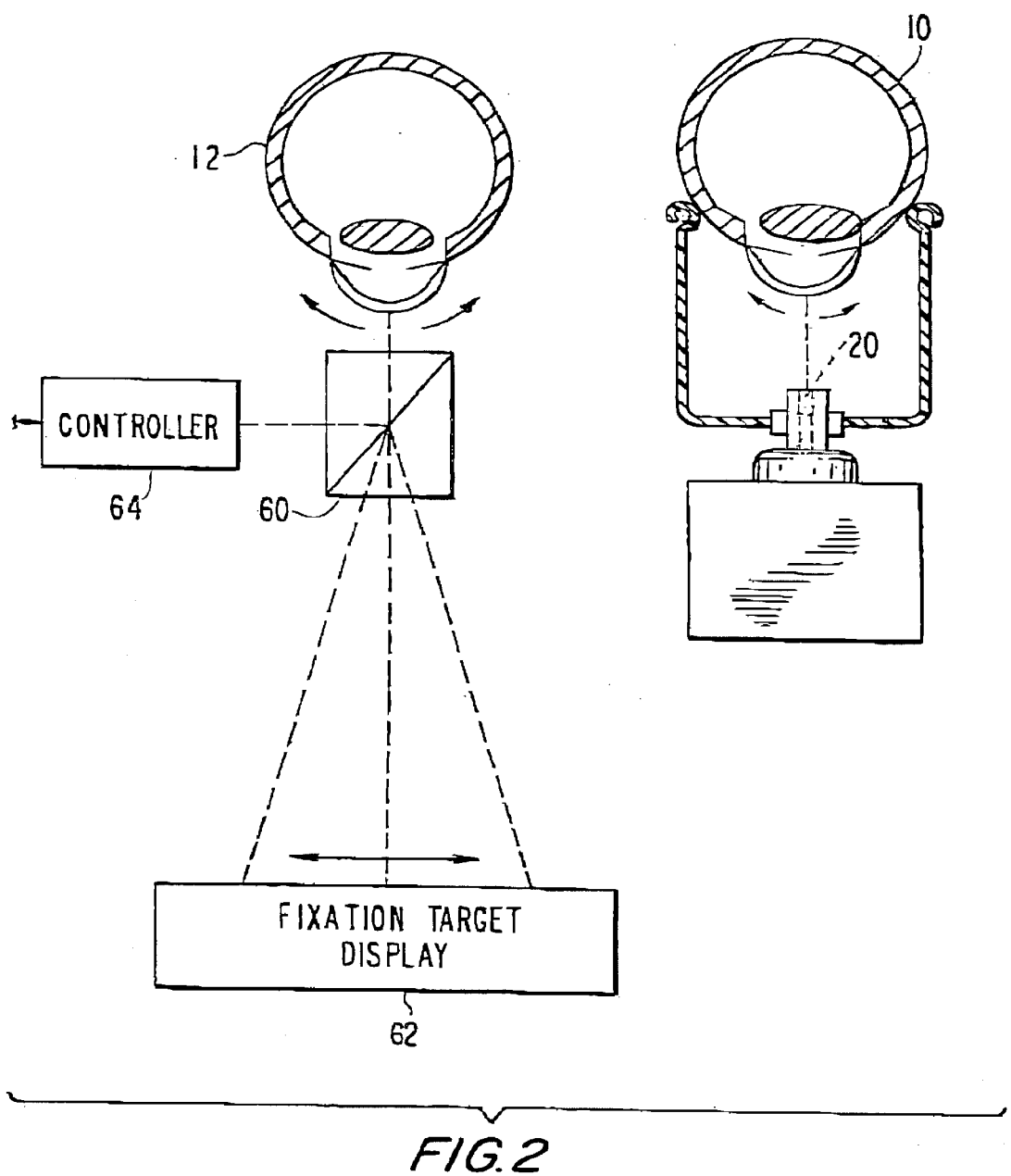
FIG. 2 is a side elevation view similar to that of FIG. 1, illustrating another preferred embodiment of the invention.

Referring now to FIG. 2, there is schematically illustrated a further preferred embodiment where the improved scanning apparatus is operated in combination with a fixation target display that is also oriented in a vertical, upwardly-facing position. In the operation of this embodiment, a fixed ultrasound transducer (20) is placed in contact with the liquid solution (16) by inserting the transducer and its housing (26) into the aperture (35) in the bottom wall of eye cup (30), essentially as was described above in connection with FIG. 1. The transducer (20) directs a beam of ultrasound energy to the first eye (10) and receives echoes of the ultrasound energy. A fixation source (60) is juxtaposed to the second eye (12) of the subject and displays a fixation target (62). A controller (64) operates the fixation source to move the fixation target relative to the second eye, while the subject moves the second eye (12) so as to remain focused on the fixation target. The movement of the second eye causes the first eye to move concurrently and enables relative movement between the beam of ultrasound energy emanating from the fixed source of transducer (20) and the anterior segments of the first eye (10), thereby providing a superior biometric display.

In a further preferred embodiment, an optical lens is positioned below one or both eyes to receive and transmit an image of either or both the first examined eye or the second eye via, e.g., optical fiber, for display on a television monitor to thereby allow the operator to visualize the process.

Figure 3:
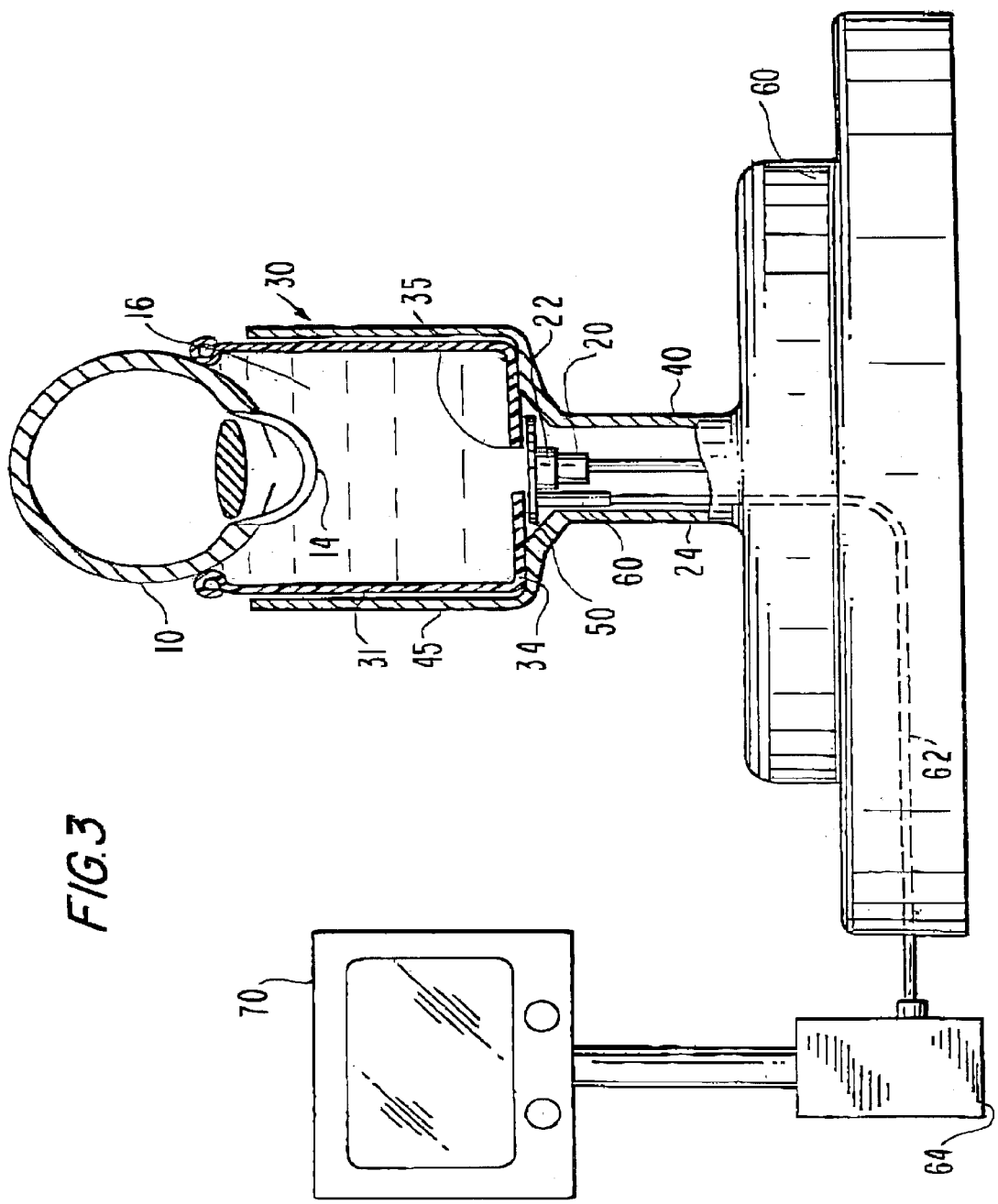
FIG. 3 is a side elevation view, partly in cross-section, schematically illustrating yet another preferred embodiment of the invention.

With reference to FIG. 3, a second preferred embodiment of an eye cup for use with the invention is illustrated. The eye cup (30) is of a structure similar to that described above in connection with FIG. 1, but with the important distinction that the aperture (35) in the bottom wall (34) of the eye cup is rendered fluid-tight by virtue of a membrane that is capable of transmitting the ultrasonic waves generated by the transducer element (22). Because the transmission losses of the ultrasonic energy through the atmosphere are unacceptable, the membrane (50) is placed in contact with the transducer emitting element (22). Upon activation of the transducer, the ultrasonic energy is transmitted via the membrane (50) to the solution (16) in accordance with the procedures described above.

The construction and method of the invention as illustrated in FIG. 3 provides the advantages of permitting the removal of the cup (30) from the apparatus to empty the liquid contents after the procedure, and to either sterilize the cup or to produce it from materials that will render it economically disposable.

The membrane (30) preferably fabricated from a resilient material that can withstand the forces generated by the transducer and reflected waves as well as the weight of the saline solution for the duration of at least one typical procedure. The configuration of the transducer element must also take into account its contact with a resilient material and it should not have sharp edges or corners that may puncture or rapidly wear the membrane. A suitable polymeric material is saran, or poly vinylidene chloride The membrane can be secured in position to form a fluid-tight seal on the bottom of the cup using adhesives, ultrasonic welding methods or mechanical means, in accordance with techniques well known in the industrial arts.

In a further preferred embodiment illustrated in FIGS. 3 and 4, a video optical lens (60) is positioned proximate the transducer in order to capture an image of the cornea and transmit it via transmission means (62), e.g., optical fibers, to a camera (64) and to a monitor (70) for viewing.

As also shown in FIG. 3, the sidewalls of the eye cup supporting member (45) extend upwardly terminating proximate the rim (32) of eye cup (30) to provide the support necessary for a lighter-weight disposable cup. The eye cup is preferably produced from a thermosetting polymer that is heat resistant and can be sterilized repeatedly for the non-disposable embodiment. Polymers such as PVC and others that have been used in the medical field can be employed. The entire body of the cup in the first embodiment described above is preferably produced in integral molded form, but with a separate gasket that can be removed and replaced in the event of wear and leaking, or to maintain a sterile environment.

In order to expedite the setup of the apparatus employing a disposable eye cup, the eye cups are preferably supplied in a sterile condition sealed in a sterile transparent wrapper that is sufficiently flexible to permit the user to firmly grasp the interior and exterior sidewall between the thumb and fingers of one hand while tearing the package open to free the container, thereby allowing the user to place the sterile cup into the cup holder (45) without touching the cup. The setup is completed by addition of the sterile saline solution to the cup.

FIG. 4 illustrates one preferred arrangement of the apparatus for use by a subject that is ambulatory, or one who is in a wheelchair. With the apparatus set up on a stable surface (100), e.g., a table top, that is approximately waist high, the subject (105) is seated comfortably in a chair (110) in an upright position, thereby avoiding the potential difficulties and discomfort associated with lying supine on an examination table under what can appear as a somewhat threatening piece of apparatus suspended over the eye. The experience of the subject in using the apparatus and method of the invention is more akin to looking into the eyepiece of a microscope by simply lowering the head at the neck to place the eye over the rim of the cup. Since no physical discomfort can be perceived by the subject through the anesthetized eye, the potential stress and psychological trauma associated with the procedure is minimized. The subject's head can be stabilized in an adjustable head support (80), which can take the form of an assembly comprising a chin supporting cup (82), adjustably received in base member (84) and secured in position by release means (86). The head support (80) can also take the form of a contoured support for the subject's forehead and support (80) can be joined to, or separate from the apparatus (1). The head support (80) can optionally include a strap or similar restraint to assist in maintaining stability during the scanning.

We claim:

1. An improved apparatus for ultrasonically scanning the cornea of a human subject's eye by means of a transducer element that transmits ultrasonic waves through a liquid conducting medium in contact with the cornea and a receiver for plotting the reflected ultrasonic waves, the improvement comprising:
    a transducer housing for positioning the transducer in a fixed upwardly facing a vertically aligned position;
    a transducer mounted in said transducer housing;
    an upwardly opening eye cup mounted on the transducer housing for receiving the liquid conducting medium, the eye cup having an upper end forming a contact rim, the upper contact rim of the eye in facing upwardly to receive the surface of the subject's eye in touching alignment, the lower end of the eye cup configured to maintain operative contact between the transducer element and the liquid contents of the eye cup, whereby the subjects cornea and adjacent tissue is lowered into contact with the rim of the eye cup from a position directly above the eye cup.

2. The apparatus of claim 1 where the eye cup is disposable.

3. The apparatus of claim 2 where the disposable eye cup is sterilizable.

4. The apparatus of claim 2 which further comprises an eye cup support member secured to the transducer housing for receiving the disposable eye cup.

5. The apparatus of claim 2 where the disposable eye cup comprises a vertically extending sidewall terminating in a cup base mounting member for cooperatively engaging the exterior side wall of the transducer housing in aligned fluid-tight relation.

6. The apparatus of claim 2 where the disposable eye cup comprises a fluid-tight container having a continuous sidewall and a base member formed from an ultrasonically conductive membrane.

7. The apparatus of claim 1 which further comprises a fluid-tight seal disposed between the base of the eye cup support member and the transducer housing.

8. The apparatus of claim 1 where the transducer element is in communication with the interior of the eye cup, whereby during scanning the transducer element is immersed in the liquid contained by the eye cup.

9. The apparatus of claim 8 further comprising one or more optically reflective members for directing parallel beams of light toward the subject's eyes, one of said beams being directed proximate to and in vertical alignment with the vertical axis of the transducer housing.

10. The apparatus of claim 1 which further comprises an ultrasonically conductive membrane, where the transducer element is in contact with one surface of the ultrasonically conductive membrane, the opposite surface of said membrane being contacted by the liquid contained in the eye cup.

11. The apparatus of claim 1 further comprising a vertically oriented movable fixation source disposed adjacent to the transducer housing and a controller operatively connected to the fixation source.

12. The apparatus of claim 11 which further comprises a protective cabinet.

13. The apparatus of claim 1 which further comprises an optical lens and image transmission means positioned proximate the transducer for receiving images of the cornea.

14. An improved method of performing an ultrasonic scanning of the eye of a human subject to produce a visual image, the method comprising:
   (a) providing a fixed, vertically mounted transducer housing in which is secured an upwardly facing transducer, said transducer having a transmitting element positioned proximate the open end of the transducer housing;
   (b) positioning an eye cup in fixed, fluid-tight relation to the transducer housing with the rim of the eye cup facing vertically, the interior of the eye cup in conductive communication with the transducer element;
   (c) filling the eye cup with a conductive liquid that is physiologically compatible with the human eye;
   (d) lowering the subject's cornea and surrounding tissue into contact with the rim of the eye cup from a position directly above the eye cup, to thereby immerse the subject's cornea in the conductive liquid; and
   (e) activating the transducer to generate ultrasonic waves to traverse the subject's cornea and scanning the reflected waves for imaging data.

15. The method of claim 14 where the subject is seated and the subject's head is lowered until the cornea comes into contact with the fluid contained in the eye cup.

16. The method of claim 15 where the transducer and eye cup are securely positioned on a rigid surface in front of the seated subject.

17. The method of claim 15 including the further steps of:
   providing at least one optical receiving lens and associated transmission and display means;
   positioning the at least one optical receiving lens below at least one of the subject's eyes to receive and image of the eye;
   transmitting the image received by the at least one lens to the display means,
   whereby the scanning of the subject's eye is visually monitored.

18. The method of claim 14 where the eye cup is disposable and the method comprises the further steps of:
   (f) providing an eye cup support member for receiving a disposable eye cup;
   (g) placing a disposable eye cup in the support member; and
   (h) removing and discarding the disposable eye cup after the scanning of the subject's cornea is completed.

19. A disposable eye cup for use in an apparatus for the ultrasonic scanning of the cornea of a human subject utilizing waves generated by a transducer, the eye cup comprising:
   a continuous sidewall, one end of the side wall terminating in a rim for contacting the surface of the subject's eye surrounding the cornea, the opposite end joined to a bottom wall, the bottom wall of the eye cup terminating in fluid-tight sealing means for maintaining a conductive liquid in the cup and for the transmission of ultrasonic waves from the transducer through the conductive liquid in the cup.

20. The disposable eye cup of claim 19 where the fluid-tight sealing means comprises a resilient membrane that forms an extension of the bottom wall of the cup, said membrane being aligned with respect to the cup sidewalls to transmit the waves generated by the transducer.

21. The disposable eye cup of claim 20 where the membrane is formed from the saran polymer polyvinylidene chloride.

22. The disposable eye cup of claim 19 where the fluid-tight sealing means comprises an aperture defined by the bottom wall, said aperture being axially aligned with the axis of the transducer, the periphery of the aperture forming gasket retaining means, and a gasket securely positioned in said gasket retaining means.

23. The disposable eye cup of claim 22 where the aperture is circular and the gasket is an o-ring.

24. The disposable eye cup of claim 22 where the rim, sidewall and base member are integrally molded from a heat-sterilizable polymer.

25. The disposable eye cup of claim 19 that is sterile and that further comprises a sealed transparent sterile wrapper.

* * * * *

UNITED STATES PATENT AND TRADEMARK OFFICE
CERTIFICATE OF CORRECTION

PATENT NO. : 6,315,727 B1
DATED : November 13, 2001
INVENTOR(S) : D. Jackson Coleman et al.

It is certified that error appears in the above-identified patent and that said Letters Patent is hereby corrected as shown below:

<u>Title page,</u>
Item [73], Assignee, replace "Cornel Research Foundation, Inc." with -- Cornell Research Foundation, Inc. --.

Signed and Sealed this

Third Day of December, 2002

JAMES E. ROGAN
*Director of the United States Patent and Trademark Office*